United States Patent
Hu et al.

(10) Patent No.: US 11,728,151 B2
(45) Date of Patent: Aug. 15, 2023

(54) MASS SPECTROMETRY BASED METHOD FOR DETECTING SERUM METABOLITE

(71) Applicant: SHANGHAI BIOPROFILE TECHNOLOGY CO., LTD., Shanghai (CN)

(72) Inventors: Jianwen Hu, Shanghai (CN); Jie Dai, Shanghai (CN)

(73) Assignee: SHANGHAI BIOPROFILE TECHNOLOGY CO., LTD., Shanghai (CN)

( * ) Notice: Subject to any disclaimer, the term of this patent is extended or adjusted under 35 U.S.C. 154(b) by 40 days.

(21) Appl. No.: 17/555,453

(22) Filed: Dec. 19, 2021

(65) Prior Publication Data
US 2022/0246413 A1 Aug. 4, 2022

(30) Foreign Application Priority Data
Feb. 1, 2021 (CN) .......................... 202110135510.X

(51) Int. Cl.
*H01J 49/00* (2006.01)
(52) U.S. Cl.
CPC ...... *H01J 49/0036* (2013.01); *H01J 49/0031* (2013.01)
(58) Field of Classification Search
CPC .... H01J 49/0036; H01J 49/0031; H01J 49/26; G01N 33/6848; G01N 30/06; G01N 30/72; H04L 63/0876
USPC .................................................. 250/281, 282
See application file for complete search history.

(56) References Cited

U.S. PATENT DOCUMENTS

2018/0024108 A1\* 1/2018 Cooks .................. H01J 49/424
250/282

\* cited by examiner

*Primary Examiner* — Michael Maskell

(57) ABSTRACT

The present disclosure discloses a mass spectrometry based method for detecting serum metabolite, and relates to the technical field of mass spectrometric detection. The method includes: analyzing detection matching values of detection personnels receiving a detection task, and selecting a detection personnel with the largest detection matching value as a selected detection personnel; firstly performing position matching, then performing configuration to obtain a serum sample, and performing mass spectrometric detection on the serum sample after the selected detection personnel reaches a detection position; verifying a fingerprint of the selected detection personnel before the selected detection personnel uploads mass spectrometric result data; and stamping the mass spectrometric result data with a time mark and uploading the mass spectrometric result data to a detection platform for storage by the selected detection personnel through a mobile phone terminal after the fingerprint verification is passed, ensuring the authenticity and safety of the data.

4 Claims, 1 Drawing Sheet

Log in a detection platform and issue a detection task on the detection platform by an operator, and access the detection platform and receive the detection task by detection personnels through mobile phone terminals Analyze detection matching values of the detection personnels receiving the detection task, select a detection personnel with the largest detection matching value as a selected detection personnel for the detection task; and send the detection task to the mobile phone terminal of the selected detection personnel Perform configuration to obtain a serum sample and perform mass spectrometric detection on the serum sample after the selected detection personnel reaches the detection position; analyze a mass spectrometric detection result, to obtain mass spectrometric result data; and send, by the selected detection personnel, the mass spectrometric result data to the detection platform for storage Send, by a user through an intelligent terminal, a data inquiry instruction to the detection platform, and trace a source of the data inquiry instruction and verify an internet protocol (IP) network address and a signal source position by the detection platform Log in a detection platform and issue a detection task on the detection platform by an operator, and access the detection platform and receive the detection task by detection personnels through mobile phone terminals Analyze detection matching values of the detection personnels receiving the detection task, select a detection personnel with the largest detection matching value as a selected detection personnel for the detection task; and send the detection task to the mobile phone terminal of the selected detection personnel Perform configuration to obtain a serum sample and perform mass spectrometric detection on the serum sample after the selected detection personnel reaches the detection position; analyze a mass spectrometric detection result, to obtain mass spectrometric result data; and send, by the selected detection personnel, the mass spectrometric result data to the detection platform for storage Send, by a user through an intelligent terminal, a data inquiry instruction to the detection platform, and trace a source of the data inquiry instruction and verify an internet protocol (IP) network address and a signal source position by the detection platform

MASS SPECTROMETRY BASED METHOD FOR DETECTING SERUM METABOLITE

CROSS REFERENCE TO THE RELATED APPLICATIONS

This application is based upon and claims priority to Chinese Patent Application No. 202110135510.X, filed on Feb. 1, 2021, the entire contents of which are incorporated herein by reference.

FIELD OF TECHNOLOGY

The present disclosure relates to the technical field of mass spectrometric detection, and in particular to a mass spectrometry based method for detecting serum metabolite.

BACKGROUND

Matrix-assisted laser desorption ionization time-of-flight mass spectrometry technology, namely MALDI-TOF-MS, is a new type of soft ionization organic mass spectrometry technology developed in the 1980s. This technology has the characteristics of high sensitivity, high resolution, high accuracy, low sample consumption, rapid and high-throughput detection and the like. The basic principle of MALDI-TOF-MS detection is: the sample to be tested is dispersed in the matrix to form a co-crystal, when irradiated with a laser, the matrix absorbs energy from the laser and transitions to an excited state, the excited state is unstable, the matrix transfers energy to the sample molecules and then returns to the ground state, the sample molecules absorb energy, ionize and vaporize to form charged ions. After the ions are accelerated by a strong electric field, the charged ions are separated by a mass analyzer, and finally enter the detector. According to the different mass-to-charge ratios of the ions, a large amount of specific peak information is detected to form a mass spectrum. Since biological molecules such as nucleic acids, proteins and polysaccharides have a corresponding relationship with their molecular weights, after the mass spectrum is processed and analyzed by software, the molecular weight and structure information of various nucleic acids, proteins, polysaccharides and other substances in the sample can be obtained;

However, in the prior art, there is a problem that the corresponding inspectors cannot be reasonably allocated to perform mass spectrometry detection according to a detection matching value, resulting in low detection efficiency, and at the same time, there is a lack of security protection for mass spectrometry result data, and there is a risk of data loss and theft.

SUMMARY

An objective of the present disclosure is to provide a mass spectrometry based method for detecting serum metabolite. The present disclosure may rationally allocate a corresponding detection personnel for the mass spectrometric detection according to a detection matching value, so as to improve the detection efficiency. When a user sends a data inquiry instruction to a detection platform through an intelligent terminal, the detection platform traces a source of the data inquiry instruction and verifies an internet protocol (IP) network address and a signal source position, so as to increase the difficulty in data leakage and improve the data safety.

The objective of the present disclosure may be implemented through the following technical solution: a mass spectrometry based method for detecting serum metabolite, includes:

step 1: logging in a detection platform and issuing a detection task on the detection platform by an operator, and accessing the detection platform and receiving the detection task by detection personnels through mobile phone terminals; the detection task includes a detection position, the detection position being a position of a serum sample to be detected;

step 2: analyzing detection matching values of the detection personnels receiving the detection task, selecting a detection personnel with the largest detection matching value as a selected detection personnel for the detection task; and sending the detection task to the mobile phone terminal of the selected detection personnel;

step 3: performing configuration to obtain a serum sample and performing mass spectrometric detection on the serum sample after the selected detection personnel reaches the detection position, analyzing a mass spectrometric detection result, to obtain mass spectrometric result data; and sending, by the selected detection personnel, the mass spectrometric result data to the detection platform for storage; specifically including:

S31: taking a photo, through the mobile phone terminal, for the detection position after the selected detection personnel reaches the detection position, sending the photo and a current real-time position to the detection platform; performing position matching after the detection platform receives the current real-time position and the photo of the detection position sent by the selected detection personnel; and generating a detection start signal when the current real-time position coincides with the detection position;

S32: taking out a frozen plasma sample after the selected detection personnel receives the detection start signal, adding a certain amount of unfrozen plasma into an eppendorf (EP) tube, adding ice methanol in a volume proportion, performing scrolling and centrifugating, and adding a supernatant into a new EP tube, to obtain the serum sample;

S33: extracting the serum sample, spotting a diluted serum sample on a target plate, drying the sample at a room temperature; then preparing a matrix containing iron oxide nanoparticles, spotting the matrix containing iron oxide nanoparticles on the serum sample on the target plate, and drying at the room temperature;

S34: performing the mass spectrometric detection on a serum sample obtained from the step S33; and analyzing a mass spectrometric detection result, to obtain mass spectrometric result data; and S35: uploading, by the selected detection personnel, the mass spectrometric result data to the detection platform for the storage, specifically including: verifying a fingerprint of the selected detection personnel before the selected detection personnel uploads the mass spectrometric result data; and stamping the mass spectrometric result data with a time mark and uploading the mass spectrometric result data to the detection platform for the storage by the selected detection personnel through the mobile phone terminal after the fingerprint verification is passed; and step 4: sending, by a user through an intelligent terminal, a data inquiry instruction to the detection platform, and tracing a source of the data inquiry instruction and verifying an internet protocol (IP) network address and a signal source position by the detection platform.

Further, the analyzing detection matching values of the detection personnels receiving the detection task in step 2 specifically includes:

S21: marking the detection personnels receiving the detection task as primarily-selected personnels; sending a position acquisition instruction to mobile phone terminals of the primarily-selected personnels, acquiring positions of the primarily-selected personnels, calculating distance differences between the positions of the primarily-selected personnels and the detection position to obtain detection distances, and marking the detection distances as G1;

S22: calculating time differences between entry times of the primarily-selected personnels and a current time of a system to obtain entry time lengths, and marking the entry time lengths as T1; and setting the total numbers of detection of the primarily-selected personnels as C1; and setting ages of the primarily-selected personnels as N1;

S23: setting each of all types of mass spectrometer detectors to correspond to a preset value, matching a type of a mass spectrometer detector of an initial detection user with all the types to obtain a corresponding preset value, and marking the corresponding preset value as Y1;

S24: acquiring and analyzing operation information of the mass spectrometer detectors, to obtain operation values of the mass spectrometer detectors, and marking the operation values as F1;

S25, normalizing the detection distances, the entry time lengths, the total numbers of detection, the ages, the preset value, and the operation values, and taking numerical values thereof; and utilizing a formula $$GP = \frac{T1 \times d1 + C1 \times d2 + Y1 \times d3}{G1 \times a1 + F1 \times a2} + |N1 - 35| \times d4$$

to obtain detection matching values GP of the primarily-selected personnels, wherein a1, a2, d1, d2, d3, and d4 are coefficient factors; and S26: selecting a detection personnel with the largest detection matching value as the selected detection personnel for the detection task; sending the detection task to the mobile phone terminal of the selected detection personnel, and adding the total number of detection of the selected detection personnel by 1.

Further, the acquiring and analyzing operation information of the mass spectrometer detectors, to obtain operation values of the mass spectrometer detectors in step S24 specifically includes:

S241: obtaining the operation information of the mass spectrometer detectors, wherein the operation information includes operation start time and operation end time; and calculating time differences between the operation start time and corresponding operation end time to obtain single operation time lengths of the mass spectrometer detectors; summing all the single operation time lengths of the mass spectrometer detectors to obtain total operation time lengths, marking the total operation time lengths as CT; and setting the numbers of maintenance of the mass spectrometer detectors as C2;

S242, sequencing, in a time sequence, all the operation start time and all the operation end time of the mass spectrometer detectors; and calculating time differences between every adjacent pair of sequenced operation end time and operation start time, to obtain single operation interval time lengths;

S243, comparing the single operation interval time lengths with an interval time length threshold value; marking corresponding single operation interval time lengths as influential interval time lengths when the single operation interval time lengths are less than or equal to the interval time length threshold value; counting the number of occurrence of the influential interval time lengths, and marking the number of occurrence as C3;

S244: calculating differences between the influential interval time lengths and the interval time length threshold value to obtain front-interval values, and marking the front-interval values as Q1;

setting front-interval coefficients as Kc, where c=1, 2, ..., 20; wherein K1<K2 ... <K20, each front-interval coefficient Kc corresponds to a preset front-interval value range, the preset front-interval value ranges being (k1,k2], (k2, k3], ..., (k20,k21], and k1<k2< ... <k20<k21 in sequence;

the front-interval coefficients corresponding to the preset front-interval value ranges are Kc when Q1∈(kc,kc+1];

utilizing a formula Q2=Q1×Kc to obtain influential values Q2 corresponding to the front-interval values, summing all influential values corresponding to the front-interval values to obtain a total front-interval influential value, and marking the total front-interval influential value as Q3; and utilizing a formula GQ=C3×a3+Q3×a4 to obtain interval influential coefficients GQ, wherein a3 and a4 are coefficient factors; and S245, normalizing the total operation time lengths, the numbers of maintenance, and the interval influential coefficients, taking numerical values thereof; and utilizing a formula F1=(CT×b1+GQ×b2)/(C2×b3) to obtain operation values F1 of the mass spectrometer detectors, wherein b1, b2, and b3 are coefficient factors.

Further, for the tracing a source of the data inquiry instruction in step 4, the source tracing is to obtain the IP network address and the signal source position of the intelligent terminal sending the data inquiry instruction; the verifying an IP network address and a signal source position specifically includes:

S41: marking the intelligent terminal sending the data inquiry instruction as m, and obtaining a normal access schedule of the intelligent terminal m;

marking a time when the detection platform receives the data inquiry instruction as an access time; and matching the access time with the corresponding normal access schedule; and enabling the data inquiry instruction to be valid when the access time belongs to the corresponding normal access schedule, and enabling the data inquiry instruction to be invalid and refusing access when the access time does not belong to the corresponding normal access schedule;

S42, verifying the IP network address and the signal source position when the data inquiry instruction is valid, specifically including:

S421, obtaining a login record of the IP network address, wherein the login record includes the number of login and a login time length;

marking the number of times of logging in, by the IP network address, the detection platform in ten days before a current time of a system as a login frequency, and marking the login frequency as L1;

summing corresponding login time lengths for logging in, by the IP network address, the detection platform, to obtain a total login time length, and marking the total login time length as L2;

utilizing a formula $H1=L1\times g1+L2\times g2$ to obtain an active value H1 of the IP network address, wherein g1 and g2 are coefficient factors;

comparing the active value H1 with an active threshold value; determining that the IP network address is normal when the active value H1 is greater than or equal to the active threshold value, and continuing to conduct step S422; and determining that the IP network address is abnormal when the active value H1 is less than the active threshold value, and refusing access; and S422: obtaining a real-time signal source position of the intelligent terminal and historical signal source positions of the intelligent terminal in ten days before the current time of the system, marking all the historical signal source positions within a radius R by taking the real-time signal source position as a center, and considering the historical signal source positions and the real-time signal source position as the same position;

counting the number of occurrence of the signal source positions at the same position and marking the number of occurrence as a signal source frequency P1;

comparing the signal source frequency P1 with a frequency threshold value; and determining that the signal source position is normal when the signal source frequency P1 is greater than or equal to the frequency threshold value, passing verification, and allowing access; otherwise determining that the signal source position is abnormal and refusing access.

The present disclosure has the beneficial effects:

1. The present disclosure includes analyzing the detection matching values of the detection personnels receiving the detection task, marking the detection personnels receiving the detection task as the primarily-selected personnels, and obtaining the detection distances, the entry time lengths, the total numbers of detection, and the ages of the primarily-selected personnels; acquiring and analyzing the operation information of the mass spectrometer detectors, to obtain the operation values of the mass spectrometer detectors; obtaining the detection matching values of the primarily-selected personnels in combination with a related algorithm, and selecting the detection personnel with the largest detection matching value as the selected detection personnel for the detection task; and sending the detection task to the mobile phone terminal of the selected detection personnel. The present disclosure can rationally allocate the corresponding detection personnel for the mass spectrometric detection according to the detection matching value, so as to improve the detection efficiency;

2. The present disclosure further includes taking the photo, through the mobile phone terminal, of the detection position after the selected detection personnel reaches the detection position, sending the photo and the current real-time position to the detection platform for position matching, so as to ensure that the detection position for the mass spectrometric detection meets requirements and ensure the authenticity of the data; then performing the configuration to obtain the serum sample and performing the mass spectrometric detection on the serum sample; analyzing the mass spectrometric detection result, to obtain the mass spectrometric result data; verifying the fingerprint of the selected detection personnel before the selected detection personnel uploads the mass spectrometric result data; and stamping the mass spectrometric result data with the time mark and uploading the mass spectrometric result data to the detection platform for the storage by the selected detection personnel through the mobile phone terminal after the fingerprint verification is passed, thereby avoiding uploading data at will by an irrelevant personnel, and ensuring the authenticity and safety of the data;

3. The present disclosure further includes tracing, by the detection platform, the source of the data inquiry instruction when the user sends the data inquiry instruction to the detection platform through the intelligent terminal, matching the access time with the normal access schedule corresponding to the intelligent terminal, and determining whether the data inquiry instruction is valid; and verifying the IP network address and the signal source position if yes, thereby increasing the difficulty in data leakage and improving the data security.

BRIEF DESCRIPTION OF THE DRAWINGS

In order to facilitate understanding by those skilled in the art, the present disclosure will be further described below with reference to the accompanying drawings.

The sole FIGURE is a schematic flow chart of the present disclosure.

DESCRIPTION OF THE EMBODIMENTS

A technical solution in the embodiments of the present disclosure will be clearly and completely described below with reference to the accompanying drawings in the embodiments of the present disclosure. It is obvious that the described embodiments are merely a part of embodiments of the present disclosure, not all of them. All other embodiments obtained by those of ordinary skill in the art on the basis of the embodiments of the present disclosure without making inventive efforts shall fall within the scope of protection of the present disclosure.

As shown in the sole FIGURE, a mass spectrometry based method for detecting serum metabolite includes:

Step 1: Log in a detection platform and issue a detection task on the detection platform by an operator, and access the detection platform and receive the detection task by detection personnels through mobile phone terminals; the detection task includes a detection position, the detection position being a position of a serum sample to be detected;

Step 2: Analyze detection matching values of the detection personnels receiving the detection task, select a detection personnel with the largest detection matching value as a selected detection personnel for the detection task; and send the detection task to the mobile phone terminal of the selected detection personnel, specifically including:

S21: Mark the detection personnels receiving the detection task as primarily-selected personnels; send a position acquisition instruction to mobile phone terminals of the primarily-selected personnels, acquire positions of the primarily-selected personnels, calculate distance differences between the positions of the primarily-selected personnels and the detection position to obtain detection distances, and mark the detection distances as G1;

S22: Calculate time differences between entry times of the primarily-selected personnels and a current time of a system to obtain entry time lengths, and mark the entry time lengths as T1; and set the total numbers of detection of the primarily-selected personnels as C1; and set ages of the primarily-selected personnels as N1;

S23: Set each of all types of mass spectrometer detectors to correspond to a preset value, match a type of a mass spectrometer detector of an initial detection user with all the types to obtain a corresponding preset value, and mark the corresponding preset value as Y1;

S24: Acquire and analyze operation information of the mass spectrometer detectors, to obtain operation values of the mass spectrometer detectors, and mark the operation values as F1, specifically including:

S241: Obtain the operation information of the mass spectrometer detectors, wherein the operation information includes operation start time and operation end time; and calculate time differences between the operation start time and corresponding operation end time to obtain single operation time lengths of the mass spectrometer detectors; sum all the single operation time lengths of the mass spectrometer detectors to obtain total operation time lengths, mark the total operation time lengths as CT; and set the numbers of maintenance of the mass spectrometer detectors as C2;

S242, Sequence, in a time sequence, all the operation start time and all the operation end time of the mass spectrometer detectors; and calculate time differences between every adjacent pair of sequenced operation end time and operation start time, to obtain single operation interval time lengths;

S243, Compare the single operation interval time lengths with an interval time length threshold value; mark corresponding single operation interval time lengths as influential interval time lengths when the single operation interval time lengths are less than or equal to the interval time length threshold value; count the number of occurrence of the influential interval time lengths, and mark the number of occurrence as C3;

S244: Calculate differences between the influential interval time lengths and the interval time length threshold value to obtain front-interval values, and mark the front-interval values as Q1;

set front-interval coefficients as Kc, where c=1, 2, . . . , 20; wherein K1<K2 . . . <K20, each front-interval coefficient Kc corresponds to a preset front-interval value range, the preset front-interval value ranges being (k1,k2], (k2, k3], . . . , (k20,k21], and k1<k2< . . . <k20<k21 in sequence;

the front-interval coefficients corresponding to the preset front-interval value ranges are Kc when Q1∈(kc,kc+1];

utilize a formula Q2=Q1×Kc to obtain influential values Q2 corresponding to the front-interval values, sum all influential values corresponding to the front-interval values to obtain a total front-interval influential value, and mark the total front-interval influential value as Q3; and utilize a formula GQ=C3×a3+Q3×a4 to obtain interval influential coefficients GQ, wherein a3 and a4 are coefficient factors, and for example, a3 is 0.59, and a4 is 0.78;

S245, Normalize the total operation time lengths, the numbers of maintenance, and the interval influential coefficients, and take numerical values thereof; and utilize a formula F1=(CT×b1+GQ×b2)/(C2×b3) to obtain operation values F1 of the mass spectrometer detectors, wherein b1, b2, and b3 are coefficient factors, for example, b1 is 0.11, b2 is 0.22, b3 is 0.47, and the larger the operation value F1 is, the lower detection accuracy of a corresponding mass spectrometer detector is.

S25: Normalize the detection distances, the entry time lengths, the total numbers of detection, the ages, the preset value, and the operation values, and take numerical values thereof; and utilize a formula $$GP = \frac{T1 \times d1 + C1 \times d2 + Y1 \times d3}{G1 \times a1 + F1 \times a2} + |N1 - 35| \times d4$$

to obtain detection matching values GP of the primarily-selected personnels, wherein a1, a2, d1, d2, d3, and d4 are coefficient factors, and for example, a1 is 1.01, a2 is 1.27, d1 is 0.21, d2 is 0.42, d3 is 0.39, and d4 is 0.19.

S26: Select a detection personnel with the largest detection matching value as the selected detection personnel for the detection task; send the detection task to the mobile phone terminal of the selected detection personnel, and add the total number of detection of the selected detection personnel by 1;

Step 3: Perform configuration to obtain a serum sample and perform mass spectrometric detection on the serum sample after the selected detection personnel reaches the detection position, analyze a mass spectrometric detection result, to obtain mass spectrometric result data; and send, by the selected detection personnel, the mass spectrometric result data to the detection platform for storage, specifically including:

S31: Take a photo, through the mobile phone terminal, for the detection position after the selected detection personnel reaches the detection position, send the photo and a current real-time position to the detection platform; perform position matching after the detection platform receives the current real-time position and the photo of the detection position sent by the selected detection personnel; and generate a detection start signal when the current real-time position coincides with the detection position; so as to ensure that the detection position for the mass spectrometric detection meets requirements and ensure the authenticity of the data.

S32: Take out a frozen plasma sample after the selected detection personnel receives the detection start signal, add a certain amount of unfrozen plasma into an eppendorf (EP) tube, add ice methanol in a volume proportion, perform scrolling and centrifugating, and add a supernatant into a new EP tube, to obtain the serum sample.

S33, Extract the serum sample, spot a diluted serum sample on a target plate, dry the sample at a room temperature; then prepare a matrix containing iron oxide nanoparticles, spot the matrix containing iron oxide nanoparticles on the serum sample on the target plate, and dry at the room temperature.

S34, Perform the mass spectrometric detection on a serum sample obtained from the step S33; and analyze a mass spectrometric detection result, to obtain mass spectrometric result data.

S35, Upload, by the selected detection personnel, the mass spectrometric result data to the detection platform for the storage, specifically including: verify a fingerprint of the selected detection personnel before the selected detection personnel uploads the mass spectrometric result data; and stamp the mass spectrometric result data with a time mark and upload the mass spectrometric result data to the detection platform for the storage by the selected detection personnel through the mobile phone terminal after the fingerprint verification is passed, thereby avoiding uploading data at will by an irrelevant person, and ensuring the authenticity and safety of the data.

Step 4: Send, by a user through an intelligent terminal, a data inquiry instruction to the detection platform, and trace a source of the data inquiry instruction and verify an internet protocol (IP) network address and a signal source position by the detection platform, thereby increasing the difficulty in data leakage and improving the data safety.

For the tracing a source of the data inquiry instruction by the detection platform, the source tracing is to obtain the IP network address and the signal source position of the intelligent terminal sending the data inquiry instruction; the verifying an IP network address and a signal source position specifically includes:

S41: Mark the intelligent terminal sending the data inquiry instruction as m; and obtain a normal access schedule of the intelligent terminal m;

mark a time when the detection platform receives the data inquiry instruction as an access time; and match the access time with the corresponding normal access schedule; and enable the data inquiry instruction to be valid when the access time belongs to the corresponding normal access schedule, and enable the data inquiry instruction to be invalid and refuse access when the access time does not belong to the corresponding normal access schedule;

S42, Verify the IP network address and the signal source position when the data inquiry instruction is valid, specifically including:

S421, Obtain a login record of the IP network address, wherein the login record includes the number of login and a login time length;

mark the number of times of logging in, by the IP network address, the detection platform in ten days before a current time of a system as a login frequency, and mark the login frequency as L1;

sum corresponding login time lengths for logging in, by the IP network address, the detection platform, to obtain a total login time length, and mark the total login time length as L2;

utilize a formula $H1=L1 \times g1+L2 \times g2$ to obtain an active value H1 of the IP network address, wherein g1 and g2 are coefficient factors, and for example, g1 is 0.45, and g2 is 0.66;

compare the active value H1 with an active threshold value, determine that the IP network address is normal when the active value H1 is greater than or equal to the active threshold value, and continue to conduct step S422; and determine that the IP network address is abnormal when the active value H1 is less than the active threshold value, and refuse access;

S422: Obtain a real-time signal source position of the intelligent terminal and historical signal source positions of the intelligent terminal in ten days before the current time of the system; mark all the historical signal source positions within a radius R by taking the real-time signal source position as a center, and consider the historical signal source positions and the real-time signal source position as the same position;

count the number of occurrence of the signal source positions at the same position and mark the number of occurrence as a signal source frequency P1;

compare the signal source frequency P1 with a frequency threshold value; and determine that the signal source position is normal when the signal source frequency P1 is greater than or equal to the frequency threshold value, pass verification, and allow access; otherwise determine that the signal source position is abnormal and refuse access.

The working principle of the present disclosure is:

During working, the mass spectrometry based method for detecting serum metabolite includes: firstly, logging in the detection platform and issuing the detection task on the detection platform by the operator, and accessing the detection platform and receiving the detection task by the detection personnels through the mobile phone terminals; analyzing the detection matching values of the detection personnels receiving the detection task, marking the detection personnels receiving the detection task as the primarily-selected personnels, and obtaining the detection distances, the entry time lengths, the total numbers of detection, and the ages of the primarily-selected personnels; acquiring and analyzing the operation information of the mass spectrometer detectors, to obtain the operation values of the mass spectrometer detectors; obtaining the detection matching values of the primarily-selected personnels in combination with the related algorithm, and selecting the detection personnel with the largest detection matching value as the selected detection personnel for the detection task; and sending the detection task to the mobile phone terminal of the selected detection personnel. The present disclosure can rationally allocate a corresponding detection personnel for the mass spectrometric detection according to the detection matching value, so as to improve the detection efficiency.

The present disclosure further includes: taking the photo, through the mobile phone terminal, for the detection position after the selected detection personnel reaches the detection position, sending the photo and the current real-time position to the detection platform for position matching, so as to ensure that the detection position for the mass spectrometric detection meets the requirements and ensure the authenticity of the data; then performing the configuration to obtain the serum sample and performing the mass spectrometric detection on the serum sample; analyzing the mass spectrometric detection result, to obtain the mass spectrometric result data; verifying the fingerprint of the selected detection personnel before the selected detection personnel uploads the mass spectrometric result data; and stamping the mass spectrometric result data with the time mark and uploading the mass spectrometric result data to the detection platform for the storage by the selected detection personnel through the mobile phone terminal after the fingerprint verification is passed, thereby avoiding uploading the data at will by the irrelevant person, and ensuring the authenticity and the safety of the data.

The present disclosure further includes sending, by the user through the intelligent terminal, the data inquiry instruction to the detection platform, tracing, by the detection platform, the source of the data inquiry instruction, matching the access time with the normal access schedule corresponding to the intelligent terminal, and determining whether the data inquiry instruction is valid; and verifying the IP network address and the signal source position if yes, thereby increasing the difficulty in data leakage and improving the data security.

The formulas and the coefficient factors described above are all obtained by acquiring massive data for software simulation and by setting parameters by corresponding experts, thereby being consistent with real results.

The preferred embodiments of the present disclosure disclosed above are only used to assist in the description of the present disclosure. The preferred embodiments neither describe all the details in detail, nor limit the present disclosure to the specific implementations. It is obvious that various modifications and changes may be made to the content of the description. The present disclosure selects and specifically describe these embodiments with the purpose of better explain the principle and practical use of the present disclosure, such that those skilled in the art can well understand and utilize the present disclosure. The present disclosure is only limited by the claims and the entire scope and equivalent thereof.

What is claimed is:

1. A mass spectrometry based method for detecting serum metabolite, comprising:
   step 1: logging in a detection platform and issuing a detection task on the detection platform by an operator, and accessing the detection platform and receiving the detection task by detection personnels through mobile phone terminals; the detection task comprises a detection position, the detection position being a position of a serum sample to be detected;
   step 2: analyzing detection matching values of the detection personnels receiving the detection task, selecting a detection personnel with the largest detection matching value as a selected detection personnel for the detection task; and sending the detection task to the mobile phone terminal of the selected detection personnel;
   step 3: performing configuration to obtain a serum sample and performing mass spectrometric detection on the serum sample after the selected detection personnel reaches the detection position; analyzing a mass spectrometric detection result to obtain mass spectrometric result data; and sending, by the selected detection personnel, the mass spectrometric result data to the detection platform for storage, specifically comprising:
   S31: taking a photo, through the mobile phone terminal, for the detection position after the selected detection personnel reaches the detection position, sending the photo and a current real-time position to the detection platform; performing position matching after the detection platform receives the current real-time position and the photo of the detection position sent by the selected detection personnel; and generating a detection start signal when the current real-time position coincides with the detection position;
   S32: taking out a frozen plasma sample after the selected detection personnel receives the detection start signal, adding a certain amount of unfrozen plasma into an eppendorf (EP) tube, adding ice methanol in a volume proportion, performing scrolling and centrifugating, and adding a supernatant into a new EP tube, to obtain a serum sample;
   S33: extracting the serum sample, spotting a diluted serum sample on a target plate, drying the sample at a room temperature; then preparing a matrix containing iron oxide nanoparticles, spotting the matrix containing iron oxide nanoparticles on the serum sample on the target plate, and drying at the room temperature;
   S34: performing the mass spectrometric detection on a serum sample obtained from the step S33; and analyzing a mass spectrometric detection result, to obtain mass spectrometric result data; and
   S35: uploading, by the selected detection personnel, the mass spectrometric result data to the detection platform for storage, specifically comprising: verifying a fingerprint of the selected detection personnel before the selected detection personnel uploads the mass spectrometric result data; and stamping the mass spectrometric result data with a time mark and uploading the mass spectrometric result data to the detection platform for the storage by the selected detection personnel through the mobile phone terminal after the fingerprint verification is passed; and
   step 4: sending, by a user through an intelligent terminal, a data inquiry instruction to the detection platform, and tracing a source of the data inquiry instruction and verifying an internet protocol (IP) network address and a signal source position by the detection platform.

2. The mass spectrometry based method for detecting serum metabolite according to claim 1, characterized in that the analyzing detection matching values of the detection personnels receiving the detection task in step 2 specifically comprises:
   S21: marking the detection personnels receiving the detection task as primarily-selected personnels; sending a position acquisition instruction to mobile phone terminals of the primarily-selected personnels, acquiring positions of the primarily-selected personnels, calculating distance differences between the positions of the primarily-selected personnels and the detection position to obtain detection distances, and marking the detection distances as G1;
   S22: calculating time differences between entry time of the primarily-selected personnels and a current time of a system to obtain entry time lengths, and marking the entry time lengths as T1; and
   setting the total numbers of detection of the primarily-selected personnels as C1; and setting ages of the primarily-selected personnels as N1;
   S23: setting each of all types of mass spectrometer detectors to correspond to a preset value, matching a type of a mass spectrometer detector of an initial detection user with all the types to obtain a corresponding preset value, and marking the corresponding preset value as Y1;
   S24: acquiring and analyzing operation information of the mass spectrometer detectors, to obtain operation values of the mass spectrometer detectors; and marking the operation values as F1;
   S25, normalizing the detection distances, the entry time lengths, the total numbers of detection, the ages, the preset value, and the operation values, and taking numerical values thereof; and
   utilizing a formula $$GP = \frac{T1 \times d1 + C1 \times d2 + Y1 \times d3}{G1 \times a1 + F1 \times a2} + |N1 - 35| \times d4$$

to obtain detection matching values GP of the primarily-selected personnels, wherein a1, a2, d1, d2, d3, and d4 are coefficient factors; and
   S26: selecting a detection personnel with the largest detection matching value as the selected detection personnel for the detection task; sending the detection task to the mobile phone terminal of the selected detection personnel, and adding the total number of detection of the selected detection personnel by 1.

3. The mass spectrometry based method for detecting serum metabolite according to claim 2, characterized in that the acquiring and analyzing operation information of the mass spectrometer detectors, to obtain operation values of the mass spectrometer detectors in step S24 specifically comprises:
   S241: obtaining the operation information of the mass spectrometer detectors, the operation information comprises operation start time and operation end time; and calculating time differences between the operation start time and corresponding operation end time to obtain single operation time lengths of the mass spectrometer detectors; summing all the single operation time lengths of the mass spectrometer detectors to obtain total operation time lengths, marking the total operation time lengths as CT; and setting the numbers of maintenance of the mass spectrometer detectors as C2;

S242; sequencing, in a time sequence, all the operation start time and all the operation end time of the mass spectrometer detectors; and calculating time differences between every adjacent pair of sequenced operation end time and operation start time, to obtain single operation interval time lengths;

S243: comparing the single operation interval time lengths with an interval time length threshold value; marking corresponding single operation interval time lengths as influential interval time lengths when the single operation interval time lengths are less than or equal to the interval time length threshold value; counting the number of occurrence of the influential interval time lengths, and marking the number of occurrence as C3;

S244: calculating differences between the influential interval time lengths and the interval time length threshold value to obtain front-interval values, marking the front-interval values as Q1;

and setting front-interval coefficients as Kc, where c=1, 2, ..., 20; wherein K1<K2 ... <K20; each front-interval coefficient Kc corresponds to a preset front-interval value range, the preset front-interval value ranges being (k1,k2], (k2, k3], ..., (k20,k21], k1<k2< ... <k20<k21 in sequence;

the front-interval coefficients corresponding to the preset front-interval value ranges are Kc when Q1∈(kc,kc+1];

utilizing a formula Q2=Q1×Kc to obtain influential values Q2 corresponding to the front-interval values, summing all influential values corresponding to the front-interval values to obtain a total front-interval influential value, and marking the total front-interval influential value as Q3; and utilizing a formula GQ=C3×a3+Q3×a4 to obtain interval influential coefficients GQ, wherein a3 and a4 are coefficient factors; and S245: normalizing the total operation time lengths, the numbers of maintenance, and the interval influential coefficients, and taking numerical values thereof; and utilizing a formula F1=(CT×b1+GQ×b2)/(C2×b3) to obtain operation values F1 of the mass spectrometer detectors, wherein b1, b2, and b3 are coefficient factors.

4. The mass spectrometry based method for detecting serum metabolite according to claim 1, characterized in that, for the tracing a source of the data inquiry instruction by the detection platform in step 4, the source tracing is to obtain the IP network address and the signal source position of the intelligent terminal sending the data inquiry instruction; the verifying an IP network address and a signal source position specifically comprises:

S41: marking the intelligent terminal sending the data inquiry instruction as m; and obtaining a normal access schedule of the intelligent terminal m;

marking a time when the detection platform receives the data inquiry instruction as an access time; and matching the access time with the corresponding normal access schedule;

enabling the data inquiry instruction to be valid when the access time belongs to the corresponding normal access schedule, and enabling the data inquiry instruction to be invalid and refusing access when the access time does not belong to the corresponding normal access schedule;

S42: verifying the IP network address and the signal source position when the data inquiry instruction is valid, specifically comprises:

S421: obtaining a login record of the IP network address; the login record comprises the number of login and a login time length;

marking the number of times of logging in, by the IP network address, the detection platform in ten days before a current time of a system as a login frequency; and marking the login frequency as L1;

summing corresponding login time lengths for logging in, by the IP network address, the detection platform, to obtain a total login time length, and marking the total login time length as L2;

utilizing a formula H1=L1×g1+L2×g2 to obtain an active value H1 of the IP network address, wherein g1 and g2 are coefficient factors;

comparing the active value H1 with an active threshold value; determining that the IP network address is normal when the active value H1 is greater than or equal to the active threshold value, and continuing to conduct step S422; and determining that the IP network address is abnormal when the active value H1 is less than the active threshold value, and refusing access;

S422: obtaining a real-time signal source position of the intelligent terminal and historical signal source positions of the intelligent terminal in ten days before the current time of the system; marking all the historical signal source positions within a radius R by taking the real-time signal source position as a center, and considering the historical signal source positions and the real-time signal source position as the same position;

counting the number of occurrence of the signal source positions at the same position and marking the number of occurrence as a signal source frequency P1;

comparing the signal source frequency P1 with a frequency threshold value; and determining that the signal source position is normal when the signal source frequency P1 is greater than or equal to the frequency threshold value, passing verification, and allowing access; otherwise determining that the signal source position is abnormal and refusing access.

* * * * *